(12) United States Patent
Li et al.

(10) Patent No.: US 8,744,543 B2
(45) Date of Patent: *Jun. 3, 2014

(54) SYSTEM AND METHOD FOR REMOVING ARTIFACTS FROM WAVEFORMS

(75) Inventors: Li Li, Petaluma, CA (US); Paul Mannheimer, Danville, CA (US)

(73) Assignee: Covidien LP, Mansfield, MA (US)

(*) Notice: Subject to any disclaimer, the term of this patent is extended or adjusted under 35 U.S.C. 154(b) by 1022 days.

This patent is subject to a terminal disclaimer.

(21) Appl. No.: 12/785,295

(22) Filed: May 21, 2010

(65) Prior Publication Data

US 2010/0234696 A1  Sep. 16, 2010

Related U.S. Application Data

(63) Continuation of application No. 11/241,509, filed on Sep. 29, 2005, now Pat. No. 7,725,147.

(51) Int. Cl.
*A61B 5/1455* (2006.01)
*A61B 5/02* (2006.01)

(52) U.S. Cl.
USPC ............................. 600/336; 600/323; 600/500

(58) Field of Classification Search
USPC .................. 600/310, 322, 323, 336, 500, 502
See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |

(Continued)

FOREIGN PATENT DOCUMENTS

| | | |
|---|---|---|
| DE | 19640807 | 9/1997 |
| EP | 0630203 | 12/1994 |

(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

(Continued)

*Primary Examiner* — Eric Winakur
(74) *Attorney, Agent, or Firm* — Fletcher Yoder PC (57) ABSTRACT

A technique is provided for processing a physiological signal to compensate for artifacts. The technique includes identifying artifacts within the physiological signal. The technique also includes performing one or more multi-resolution decompositions, such as wavelet transformations, on the physiological signal and compensating for the identified artifacts in some or all of the respective decomposition components. The modified decomposition components may be reconstructed to generate an artifact-compensated signal which may be provided to a monitor or other device which is otherwise not configured to compensate for signal artifacts.

20 Claims, 4 Drawing Sheets

(56) References Cited

U.S. PATENT DOCUMENTS

| | | | |
|---|---|---|---|
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,521,851 A | 5/1996 | Wei et al. | |
| 5,553,614 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,645,059 A | 7/1997 | Fein et al. | |
| 5,645,060 A | 7/1997 | Yorkey | |
| 5,680,857 A | 10/1997 | Pelikan et al. | |
| 5,692,503 A | 12/1997 | Keunstner | |
| 5,730,124 A | 3/1998 | Yamauchi | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,094,592 A | 7/2000 | Yorkey et al. | |
| 6,120,460 A | 9/2000 | Abreu | |
| 6,134,460 A | 10/2000 | Chance | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,222,189 B1 | 4/2001 | Misner et al. | |
| 6,230,035 B1 | 5/2001 | Aoyagi et al. | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,361,501 B1 | 3/2002 | Amano et al. | |
| 6,393,311 B1 | 5/2002 | Edgar, Jr. et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,519,486 B1 | 2/2003 | Edgar, Jr. et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,580,086 B1 | 6/2003 | Schulz et al. | |
| 6,584,336 B1 | 6/2003 | Ali et al. | |
| 6,591,122 B2 | 7/2003 | Schmitt | |
| 6,594,513 B1 | 7/2003 | Jobsis et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,622,095 B2 | 9/2003 | Kobayashi et al. | |
| 6,650,918 B2 | 11/2003 | Terry | |
| 6,654,621 B2 | 11/2003 | Palatnik et al. | |
| 6,654,623 B1 | 11/2003 | Kastle | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,701,170 B2 | 3/2004 | Stetson | |
| 6,708,048 B1 | 3/2004 | Chance | |
| 6,711,424 B1 | 3/2004 | Fine et al. | |
| 6,711,425 B1 | 3/2004 | Reuss | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,810,277 B2 | 10/2004 | Edgar, Jr. et al. | |
| 6,829,496 B2 | 12/2004 | Nagai et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,931,269 B2 | 8/2005 | Terry | |
| 6,939,307 B1 | 9/2005 | Dunlop | |
| 6,947,780 B2 | 9/2005 | Scharf | |
| 6,949,081 B1 | 9/2005 | Chance | |
| 6,961,598 B2 | 11/2005 | Diab | |
| 6,983,178 B2 | 1/2006 | Fine et al. | |
| 6,987,994 B1 | 1/2006 | Mortz | |
| 6,993,371 B2 | 1/2006 | Kiani et al. | |
| 6,996,427 B2 | 2/2006 | Ali et al. | |
| 7,020,507 B2 | 3/2006 | Scharf et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,679 B2 | 4/2006 | Addison et al. | |
| 7,035,697 B1 | 4/2006 | Brown | |
| 7,047,056 B2 | 5/2006 | Hannula et al. | |
| 7,072,702 B2 | 7/2006 | Edgar, Jr. et al. | |
| 7,079,880 B2 | 7/2006 | Stetson | |
| 7,127,278 B2 | 10/2006 | Melker et al. | |
| 7,162,306 B2 | 1/2007 | Caby et al. | |
| 7,209,775 B2 | 4/2007 | Bae et al. | |
| 7,215,984 B2 | 5/2007 | Diab et al. | |
| 7,215,986 B2 | 5/2007 | Diab et al. | |
| 7,225,013 B2 | 5/2007 | Geva et al. | |
| 7,236,811 B2 | 6/2007 | Schmitt | |
| 7,254,433 B2 | 8/2007 | Diab et al. | |
| 7,263,395 B2 | 8/2007 | Chan et al. | |
| 7,272,426 B2 | 9/2007 | Schmid | |
| 7,328,053 B1 | 2/2008 | Diab et al. | |
| 7,336,982 B2 | 2/2008 | Yoo | |
| 7,343,187 B2 | 3/2008 | Stetson | |
| 7,373,193 B2 | 5/2008 | Al-Ali et al. | |
| 7,376,453 B1 | 5/2008 | Diab et al. | |
| 7,383,070 B2 | 6/2008 | Diab et al. | |
| 7,398,115 B2 | 7/2008 | Lynn | |
| 2001/0005773 A1 | 6/2001 | Larsen et al. | |
| 2001/0020122 A1 | 9/2001 | Steuer et al. | |
| 2001/0039376 A1 | 11/2001 | Steuer et al. | |

(56) References Cited

U.S. PATENT DOCUMENTS

| | | |
|---|---|---|
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2003/0225337 A1 | 12/2003 | Scharf et al. |
| 2004/0010188 A1 | 1/2004 | Wasserman |
| 2004/0054270 A1 | 3/2004 | Pewzner et al. |
| 2004/0054281 A1 | 3/2004 | Adam et al. |
| 2004/0059210 A1 | 3/2004 | Stetson |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0193065 A1 | 9/2004 | Houben |
| 2004/0230106 A1 | 11/2004 | Schmitt et al. |
| 2005/0033129 A1 | 2/2005 | Edgar, Jr. et al. |
| 2005/0049470 A1 | 3/2005 | Terry |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0192493 A1 | 9/2005 | Wuori |
| 2005/0203357 A1 | 9/2005 | Debreczeny et al. |
| 2005/0209517 A1 | 9/2005 | Diab et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0200016 A1 | 9/2006 | Diab et al. |
| 2006/0211930 A1 | 9/2006 | Scharf et al. |
| 2006/0217609 A1 | 9/2006 | Diab et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0258927 A1 | 11/2006 | Edgar, Jr. et al. |
| 2006/0293574 A1 | 12/2006 | Norris |
| 2007/0004977 A1 | 1/2007 | Norris |
| 2007/0073120 A1 | 3/2007 | Li et al. |
| 2007/0213621 A1 | 9/2007 | Reisfeld et al. |
| 2007/0213622 A1 | 9/2007 | Reisfeld |
| 2007/0225581 A1 | 9/2007 | Diab et al. |
| 2007/0249918 A1 | 10/2007 | Diab et al. |
| 2007/0291832 A1 | 12/2007 | Diab et al. |
| 2008/0004514 A1 | 1/2008 | Diab et al. |
| 2008/0033266 A1 | 2/2008 | Diab et al. |
| 2008/0036752 A1 | 2/2008 | Diab et al. |
| 2008/0045823 A1 | 2/2008 | Diab et al. |

FOREIGN PATENT DOCUMENTS

| | | |
|---|---|---|
| JP | 3170866 | 7/1991 |
| JP | 3238813 | 10/1991 |
| JP | 4191642 | 7/1992 |
| JP | 4332536 | 11/1992 |
| JP | 10216115 | 8/1998 |
| JP | 2003210438 | 7/2003 |
| JP | 2003275192 | 9/2003 |
| JP | 2003339678 | 12/2003 |
| JP | 2004135854 | 5/2004 |
| JP | 2004202190 | 7/2004 |
| WO | WO9221281 | 12/1992 |
| WO | WO9403102 | 2/1994 |
| WO | WO9512349 | 5/1995 |
| WO | WO9749330 | 12/1997 |
| WO | WO9842249 | 10/1998 |
| WO | WO9842251 | 10/1998 |
| WO | WO9932030 | 7/1999 |
| WO | WO0021438 | 4/2000 |
| WO | WO0125802 | 4/2001 |
| WO | WO03000125 | 1/2003 |
| WO | WO2004075746 | 9/2004 |
| WO | WO2005009221 | 2/2005 |

OTHER PUBLICATIONS

Donoho, David L., et al.; Threshold Selection for Wavelet Shrinkage of Noisy Data, 1994.

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Donoho, David L.,; De-Noising by Soft-Thresholding, Transactions on Information Theroy, May 1995, vol. 41, No. 3.

Vincente, L.M., et al.; "Adaptive Pre-Processing of Photoplethysmographic Blood Volume Pulse Measurements," pp. 114-117 (1996).

Rusch, T., et al.; "Signal Processing Methods for Pulse Oximetry", Computers in Biology and Medicine, vol. 26, No. 2, pp. 143-159 (Mar. 1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Donoho, David L., et al.; "Robust Nonlinear Wavelet Transform Based on Median-Interpolation," Signals, Systems and Computers; Conference record of the 31st Asilomar Conference in Pacific Grove, CA; IEEE Comput. Soc., vol. 1, pp. 75-79 (1998.

Barnum, P. T., et al.; "Novel Pulse Oximetry Technology Capable of Reliable Bradycardia Monitoring in the Neonate," *Respiratory Care*, vol. 42, No. 1, p. 1072 (Nov. 1997).

Hornegger, Paulus D.; "Applied Pattern Recognition," Friedr. Vieweg & Sohn, Verlagsgesellschaft Mbh., Wiesbaden (1997), pp. 123-126.

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," Proceedings 19th International Conference IEEE/EMBS, Oct. 30-Nov. 2, 1997; pp. 2326-2329.

Cai, C., et al.; "Different Discrete Wavelet Transforms Applied to Denoising Analytical Data," J. Chem. Inf. Computer. Sci., 1998, 38, 1161-1170.

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

(56) References Cited

OTHER PUBLICATIONS

Tikkanen, P.E.; "Nonlinear Wavelet and Wavelet Packet Denoising of Electrocardiogram Signal," Biol. Cybern., 1999, vol. 80, pp. 259-267.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Kaestle, S.; "An Algorithm for Reliable Processing of Pulse Oximetry Signals Under strong Noise Conditions," *Dissertation Book*, Lubeck University, Germany (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Goutsias, John et al.,; "Nonlinear Multiresolution Signal Decomposition Schemes—Part I: Morphological Pyramids," IEEE Transactions on Image Processing, vol. 90, No. 11 (Nov. 2000), p. 15.

Heijmans, Henk J.A.M., et al.; "Nonlinear Multiresolution Signal Decomposition Schemes—Part II: Morphological Wavelets," IEEE Transactions on Image Processing, vol. 90, No. 11 (Nov. 2000), 17 pgs.

Kaestle, S.; "Determining Artefact Sensitivity of New Pulse Oximeters in Laboratory Using Signals Obtained from Patient," *Biomedizinische Technik*, vol. 45 (2000).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Macey, Katherine E.; "Wavelet Median Denoising of Ultrasound Images," Medical Imaging, Proceedings of the SPIE, vol. 4684, pp. 1151-1160 (Feb. 24, 2002).

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Salamalekis, E., et al.; "Computerized Intrapartium Diagnosis of Fetal Hypoxia Based on Fetal Heart Rate Monitoring and Fetal Pulse Oximetry Recordings Utilizing Wavelet Analysis and Neural Networks," BJOG: An International Journal of Obstetrics and Gynecology, Oct. 2002, vol. 109, pp. 1137-1142.

Sun, Yan, et al.; "ECG Signal Conditioning by Morphological Filtering," Computers in Biology and Medicine, vol. 32, No. 6, pp. 465-479 (Nov. 2002).

Cyrill, D., et al.; "Adaptive Comb Filter for Quasi-Periodic Physiologic Signals," *Proceedings of the 25$^{th}$ Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Lee, C. M. et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Yao, Jianchu, et al.; "A Novel Algorithm to Separate Motion Artifacts from Photoplethysmographic Signals Obtained With a Reflectance Pulse Oximeter," *Proceedings of the 26$^{th}$ Annual International conference of the IEEE EMBS*, San Francisco, California, Sep. 2004, pp. 2153-2156.

Matsuzawa, Y., et al.; "Pulse Oximeter," *Home Care Medicine*, pp. 42-45 (Jul. 2004); (Article in Japanese—contains English summary of article).

Yan, Yong-sheng et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Huang, J., et al.; "Low Power Motion Tolerant Pulse Oximetry," *Abstracts*, A7, p. S103. (undated).

Lang, P., et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim J.M. et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Neumann, R. et al.; "Fourier Artifact suppression Technology Provides Reliable $SpO_2$," *Abstracts*, A11, p. S105. (undated).

SYSTEM AND METHOD FOR REMOVING ARTIFACTS FROM WAVEFORMS

CROSS-REFERENCE TO RELATED APPLICATIONS

This application is a continuation of U.S. application Ser. No. 11/241,509, titled "System and Method for Removing Artifacts from Waveforms" and filed Sep. 29, 2005, the disclosure of which is hereby incorporated by reference in its entirety for all purposes.

BACKGROUND OF THE INVENTION

1. Field of the Invention

The present invention relates generally to the processing of waveform data and, more particularly, to the processing of waveforms associated with medical monitoring.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

The quality of these measurements, however, may be adversely affected by a number of factors such as patient motion, subdermal physiological structures, poor sensor operation or fit, poor signal reception and transmission, and so forth. Such factors may result in a pulse oximetry signal which contains artifacts or noise or is otherwise of low or reduced quality. When processed, such a low or reduced quality signal may result in physiological measurements being reported which may not be as accurate or reliable as desired.

To address this issue of poor signal quality, newer pulse oximetry monitors and/or systems may include algorithms, circuits, or other components to reduce, remove, or otherwise compensate for artifacts within the pulse oximetry signal. Such artifact compensation techniques, however, may be unavailable to health care providers using older or less advanced equipment that is not configured for artifact compensation. Since replacing older or less advanced pulse oximetry monitors and/or systems may not be financially feasible, a health care provider may have little choice but to continue using a system or monitor that does not compensate for artifacts in the acquired signal. However, even if an artifact compensating system is available, an older or less advanced system may still be useful within a health care facility. It may, therefore, be useful to provide artifact compensation in conjunction with the use of systems otherwise not configured to compensate for noise and artifacts with the pulse oximetry signal.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a method for processing a physiological signal, the method including the acts of: identifying one or more artifacts in a physiological signal; performing one or more multi-resolution decompositions on the physiological signal to generate two or more decomposition products; and compensating for the one or more artifacts in the two or more decomposition products to generate modified decomposition products.

There is provided one or more machine-readable media, including: a routine configured to identify one or more artifacts in a physiological signal; a routine configured to perform one or more multi-resolution decompositions on the physiological signal to generate two or more decomposition products; and a routine configured to compensate for the one or more artifacts in the two or more decomposition products to generate modified decomposition products.

There is provided a physiological monitoring system, including: a sensor configured to generate a physiological signal; and a monitor configured to receive an artifact-compensated signal derived from the physiological signal, wherein the artifact-compensated signal is generated by identifying one or more artifacts in the physiological signal, by performing one or more multi-resolution decompositions on the physiological signal to generate two or more decomposition products; by compensating for the one or more artifacts in the two or more decomposition products to generate modified decomposition products, and by reconstructing the modified decomposition products to generate the artifact-compensated signal.

There is provided a physiological sensor, including: an emitter configured to emit light; a detector configured to generate a signal in response to the emitted light; and one or more processing components configured to process the signal to generate an artifact-compensated signal.

There is provided a cable, including: one or more processing components configured to process an initial signal to generate an artifact-compensated signal.

There is provided an electronic device, including: one or more processing components configured to receive a signal generated by a physiological sensor, to process the signal to generate an artifact-compensated signal, and to transmit the artifact-compensated signal to a monitor which is not configured to perform artifact compensation

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a pulse oximeter signal (or other physiological monitor signal) from which the artifacts (such as may be generated by patient motion, subdermal physiological structures, poor sensor operation or fit, poor signal reception and transmission, and so forth) have been removed or reduced. Such a "clean" output signal may be provided as an input to a monitor or other display device which is not itself configured to compensate for signal noise or artifacts. The monitor or display device may display the clean signal or process the clean signal to generate one or more physiological characteristics of interest, such as measurements of blood oxygen level ($SpO_2$), pulse rate, and so forth. In accordance with some aspects of the present technique, the artifact and noise compensation may be performed by processing components located on the sensor itself, on a cable disposed between the sensor and the monitor or display device, or on an intermediate device, such as a conversion unit or intermediate monitor.

Figure 1:
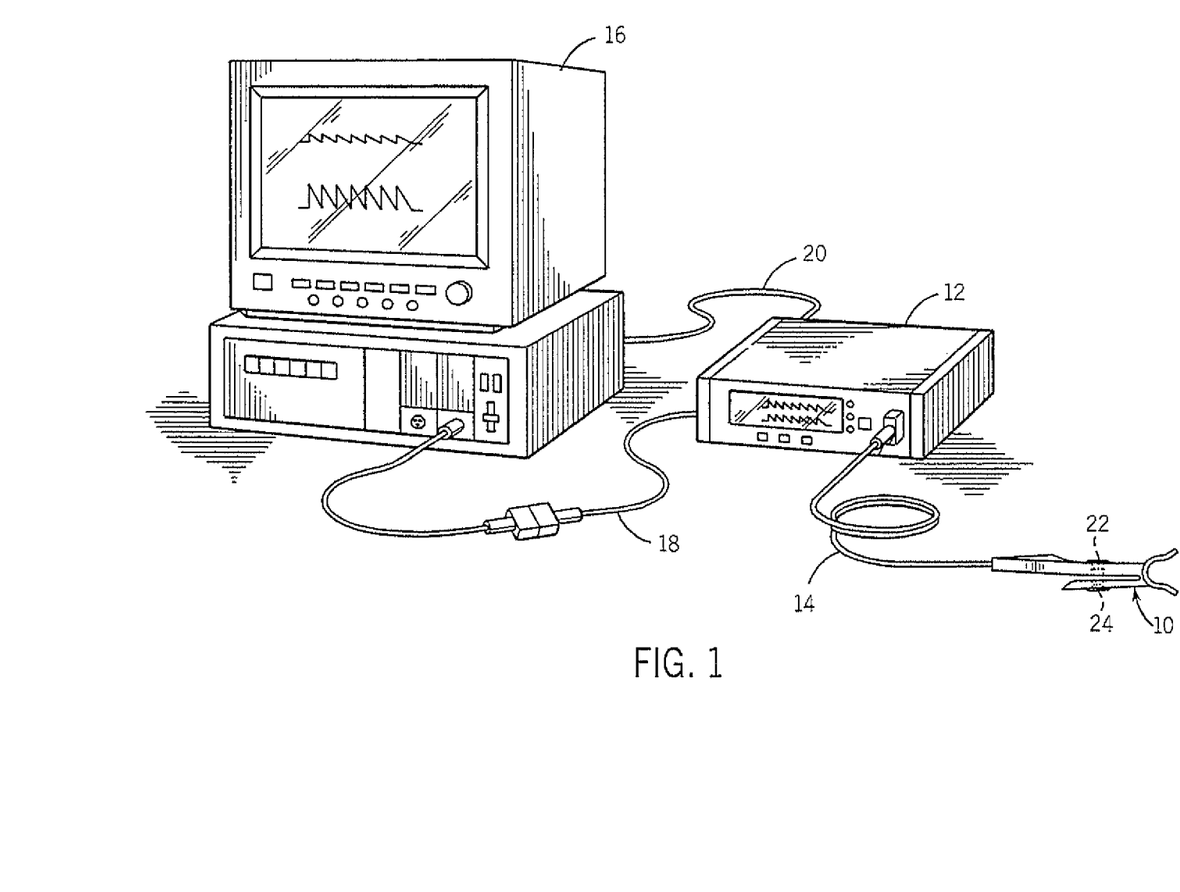
FIG. 1 illustrates a patient monitoring system coupled to a multi-parameter patient monitor and a sensor, in accordance with aspects of the present technique.

Turning now to FIG. 1, an exemplary medical monitoring system that may benefit from the present technique is depicted. The exemplary system includes a physiological sensor 10 that may be attached to a patient. The sensor 10 generates an output signal based on a monitored physiological characteristic and transmits the output signal to a patient monitor 12. In the depicted embodiment, the sensor 10 is connected to the patient monitor 12 via a cable 14 suitable for transmission of the output signal as well as any other electrical and/or optical signals or impulses communicated between the sensor 10 and monitor 12. In accordance with aspects of the present technique, the sensor 10 and/or the cable 14 may include or incorporate one or more integrated circuit devices or electrical devices, such as a memory, processor chip, or resistor, that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors. In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12.

In one embodiment, the patient monitor 12 may be a suitable pulse oximeter, such as those available from Nellcor Puritan Bennett Inc. In other embodiments, the patient monitor 12 may be a monitor suitable for measuring other physiological characteristics (such as tissue water fraction, tissue or blood carbon dioxide levels, and so forth) using spectrophotometric or other techniques. Furthermore, the monitor 12 may be a multi-purpose monitor suitable for performing pulse oximetry and/or other physiological and/or biochemical monitoring processes using data acquired via the sensor 10. Furthermore, to provide additional or enhanced functions to those performed by the monitor 12, the patient monitor 12 may be coupled to a multi-parameter patient monitor 16 via a cable 18 connected to a sensor input port and/or via a cable 20 connected to a digital communication port.

As noted above the data provided to the monitor 12 (or, alternatively, to the multi-parameter monitor 16) is generated at the sensor 10. In the example depicted in FIG. 1, the sensor 10 is an exemplary spectrophotometry sensor (such as a pulse oximetry sensor or probe) that includes an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 through which electrical and/or optical signals may be transmitted to and/or from the emitter 22 and detector 24. The sensor 10 may be configured for use with the emitter and detector on the same side of the sensor site (i.e., as a "reflectance type" sensor) or on opposite sides of the sensor site (i.e., as a "transmission type" sensor). During operation, the emitter 22 shines one or more wavelengths of light through the patient's fingertip, or other tissue, and the light received by the detector 24 is processed to determine one or more physiological characteristics of the patient.

For example, for pulse oximetry applications the oxygen saturation of the patient's arterial blood ($SaO_2$) may be determined using two or more wavelengths of light emitted by the emitter 22, most commonly red and near infrared wavelengths. After passage through the patient's tissue, a portion of the light emitted at these wavelengths is detected by the detector 24. The detector generates one or more signals, such an electrical or optical signals, in response to the amount of each wavelength that is detected at a given time. The generated signals may be digital or, where acquired as analog signals, may be digitized in implementations where digital processing and manipulation of the signals is employed. Such digitalization may be performed at the monitor 12 or prior to reaching the monitor 12. The signals, as noted above, may be transmitted via the cable 14 to the monitor 12, where the oxygen saturation or other physiological characteristic is calculated based on the signals. The signals may contain artifacts due to a variety of factors, such as light modulation by subdermal anatomic structures, patient motion during data acquisition, poor sensor operation or fit, poor signal reception and transmission, and so forth.

In one implementation of the present technique, the monitor 12 is not configured to compensate for artifacts in the data signal (such as a pulse oximetry signal) provided by the sensor 10. In such an implementation, one or more of the upstream devices or structures (such as sensor 10 and/or cable 14) may be configured to process the data to compensate for artifacts and to, thereby, generate a clean signal for processing or display by the monitor 12. Similarly, in another implementation, a downstream monitor, such as multi-parameter monitor 16 or a further downstream monitor, is not configured to compensate for artifacts in the signal. In such an implementation, the upstream devices or structures that may process the signal to compensate for artifacts may include not only the sensor 10 and/or cable 14, but also the monitors 12 or 16 and/or additional intermediate cables 18, 20. Similarly, other intermediate devices or structures may be disposed between the sensor 10 and the target monitor to process the data signal to compensate for artifacts, thereby generating a clean signal.

Figure 2:
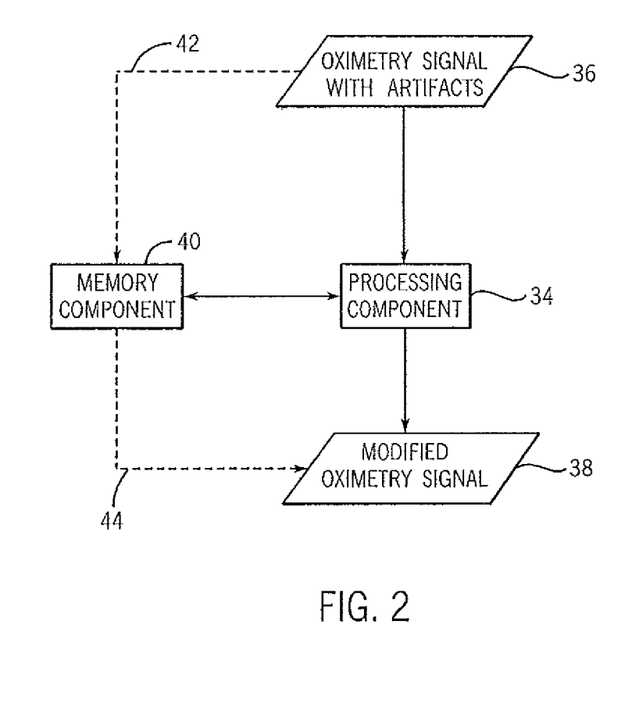
FIG. 2 is a diagram depicting components of a physiological signal processing system, in accordance with aspects of the present technique.

Referring now to FIG. 2, a box-diagram setting forth components used to process a signal to compensate for artifacts is set forth. In particular, a processing component 34 is depicted which is configured to receive an oximetry signal 36 containing artifacts and to compensate for the artifacts to produce a modified oximetry signal 38. The processing component 34 may be a general or special purpose processor or circuit suitable for incorporation into the desired structure, such as sensor 10 and/or cables 14, 18, or 20, as discussed above with regard to FIG. 1. Likewise, the processing component 34 may be a general or special purpose processor incorporated in the monitor 12, multi-parameter monitor 16, or other electronic device in the path along which the signal flows to a downstream destination that is not configured to compensate for signal artifacts.

While the processor component 34 may include hardware or circuitry designed to compensate for artifacts in the signal 36, the processor component 34 may also or alternately execute code or routines stored in a memory component 40 to accomplish the desired artifact compensation. The memory component 40 may be within the same device or structure as the processing component 34 or may be within a different structure or device in communication with the processing component 34. Such a memory components 40 may include solid state or integrated circuit type memory devices or other suitable memory devices, such as magnetic or optical media and/or drives suitable for use in the desired structure or device. As noted above, such processing components 34 and/or memory components 40 may be incorporated into the sensor 10, cables 14, 18, and 20, or the monitors 12, and 16.

FIG. 2 generally depicts that the signal 36 with artifacts is provided to the processing component 34 for artifact compensation. It is also possible, however, that the signal 36 is provided initially to the memory component 40 for subsequent processing by the processing component 34, as denoted by dotted line 42. Similarly, though the modified signal 38 may be directly output by the processing component 34 to a downstream location, it may also be stored temporarily by the memory component 40 prior to subsequent downstream transmission, as depicted by dotted line 44.

Figure 3:
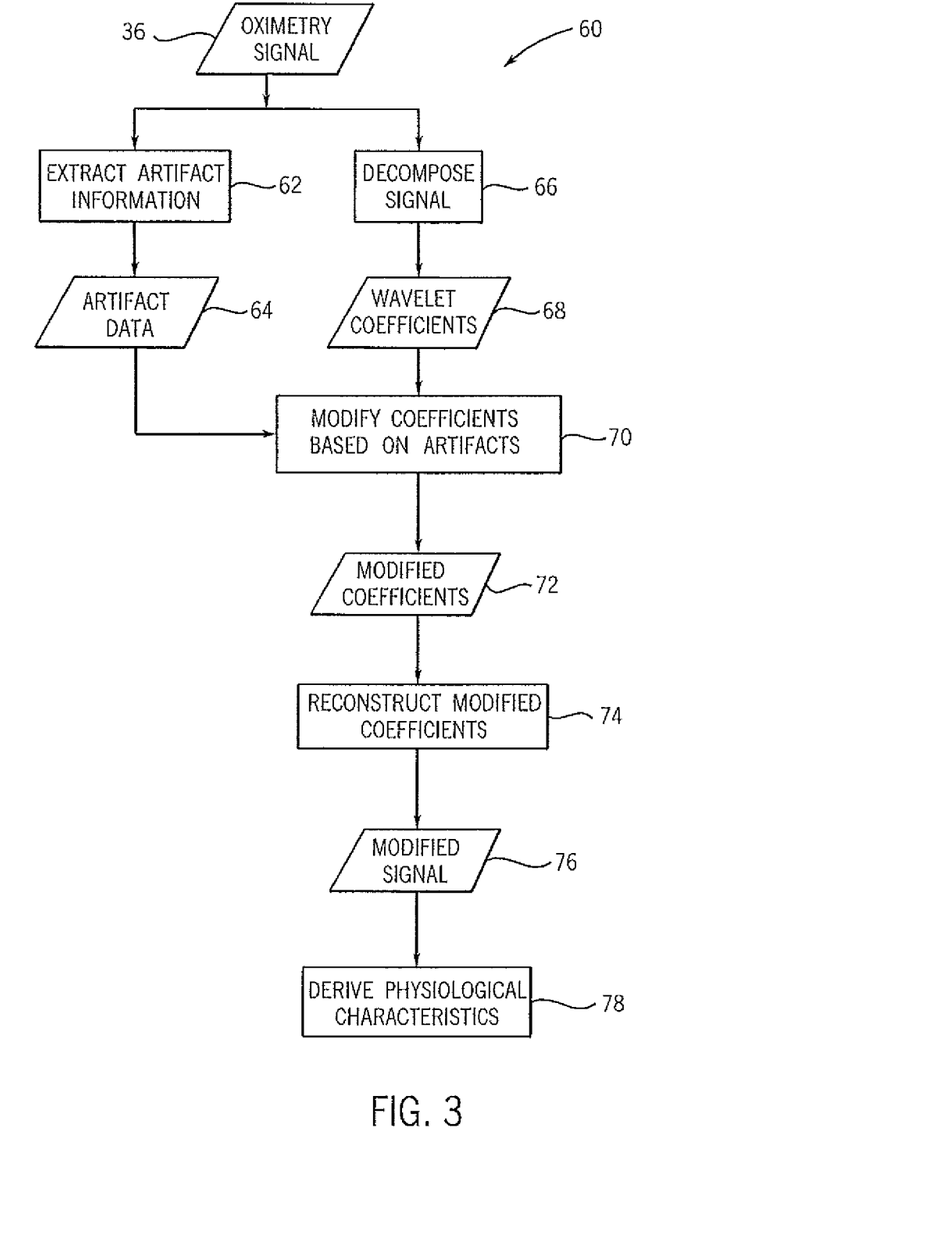
FIG. 3 is a flowchart of exemplary actions performed in accordance with aspects of the present technique.

In an embodiment of the present technique, a data signal containing artifacts is processed to compensate for those artifacts and may, subsequently, be provided to a monitor or other system that is otherwise not configured to compensate for artifacts in the signal. An example of such an embodiment is set forth in FIG. 3, depicting an artifact compensation technique 60 for use with a physiological signal. In this example, an oximetry data signal 36, such as a plethysmographic waveform, is processed to remove artifacts.

In this example, the oximetry signals 36 are processed to identify artifacts 64 within the signal (block 62). Identification of the artifacts 64 at block 62 may be accomplished by conventional artifact identification algorithms or techniques, such as may be implemented in advanced oximetry monitors or other processor-based systems commercially available or proprietary. In accordance with the present technique, these artifact identification techniques or algorithms may be implemented, as discussed above, by one or more processing components 34. These processing components 34 may be disposed within the sensor 10 itself, within the cables 14, 18, or 20 intermediate between the sensor 10 and a target monitor, and/or within an intervening monitor, such as patient monitor 12 or multi-parameter monitor 16, or other electronic device. For example, in one embodiment, the artifact identification of block 62 includes the timing and frequency of artifacts 64. This time and frequency information may be used to locate the corresponding portion of signal components within one or more wavelet decomposition levels (as discussed below) to compensate for the respective artifacts 64.

In addition, the oximetry signals 36 may be processed using a multi-resolution decomposition technique (block 66), such as wavelet decomposition by discrete wavelet transformation using a filter bank. Though wavelet transformation is discussed generally herein, those of ordinary skill in the art will appreciate that other transformation techniques capable of providing the desired time and frequency information may also be employed and are within the scope of the present technique.

As mentioned above with regard to artifact identification, the decomposition of the signal 36 may be accomplished by suitable decomposition algorithms or techniques implemented by one or more processing components 34. These processing components 34 may be disposed within the sensor 10 itself, within the cables 14, 18, or 20 intermediate between the sensor 10 and a target monitor, and/or within an intervening monitor, such as patient monitor 12 or multi-parameter monitor 16, or other electronic device. The one or more processing components 34 that implement signal decomposition may be same or different than the processing components 34 that implement artifact identification, as discussed above. Furthermore, though FIG. 3 depicts decomposition (block 66) and artifact extraction (62) implemented in parallel, other embodiments are also possible. For example, as will be appreciated by those of ordinary skill in the art, decomposition (block 66) and artifact extraction (block 62) may be implemented sequentially or in series as well.

In a wavelet decomposition implementation, each iteration of decomposition yields a low-passed signal component and a high-passed signal component represented as wavelet coefficients 68. As will be appreciated by those of ordinary skill in the art, the low-passed component generally corresponds to an approximation of the signal undergoing decomposition while the high-passed component generally corresponds to detail components of the signal undergoing decomposition. In one iterative implementation, each iteration, i.e., resolution level, of the decomposition decomposes the previous approximation, i.e., low-passed component, to generate an approximation and detail component representative of the previous approximation. In other words, the low-passed component of the previous resolution level is decomposed to yield high and low-passed components at the current resolution level. Because the low-passed components are iteratively decomposed in such an implementation, each previous resolution level may be reproduced by reintegrating the low and high-passed components (i.e., the approximation and details) of the current resolution level. Similarly, the initial signal may be reproduced by reintegrating the current resolution level of approximation and details along with previous resolution levels of detail.

During or subsequent to wavelet decomposition, some or all of the high and/or low-resolution filtered components generated at some or all of the decomposition resolution levels may be processed (block 70) to compensate for artifact signal, thereby generating modified wavelet coefficients 72. For example, the timing and frequency information for the artifacts 64 identified at block 62 may be used to deduct, remove, or modify the respective wavelet decomposition coefficients, such as during signal reconstruction, to compensate for the artifacts 64. In one embodiment, artifact compensation modifies the low-passed components (i.e., approximations) and/or the high-passed components (i.e., the details) based on the frequency and/or time information associated with the identified artifacts 64 to compensate for portions of the signal attributable to the artifacts 64 in the modified coefficients 72.

For example, in one embodiment, the oximetry signal 36 undergoes a three-stage wavelet decomposition to generate the respective high and low-passed components. In this example, artifact compensation is applied to the two high-passed bands of the three-stage decomposition to generate modified coefficients in these two bands. The artifact compensation process may involve setting applicable coefficients or portions of the signal corresponding to an artifact 64 to zero or otherwise reducing the magnitude of the applicable coefficients or portions of the signal. In this manner, the level of detail in the reconstructed signal may be reduced based on the likely correspondence of the detail level to artifacts or noise instead of to physiological signal.

The modified wavelet coefficients 72 generated by artifact compensation may be reconstructed (block 74), such as by an inverse wavelet transform, to generate a clean or artifact-compensated waveform 76. In such an embodiment, the inverse wavelet transform preserves the original physiological data while allowing artifact compensation, as opposed to techniques using synthesized waveforms (such as triangular synthetic waveforms) where physiological information may be lost. This clean waveform 76, in turn, may be processed to determine (block 78) one or more physiological characteristics of interest, such as respiratory information, blood oxygen saturation, pulse rate, and so forth. In one embodiment, the clean waveform is provided to and processed by a monitor or other electronic device what is not configured to compensate for artifacts itself. Though the preceding discussion generally discusses decomposition using wavelet transformation, other decomposition techniques that generate time-frequency and/or time-scale components may also be used in accordance with the present technique.

Figure 4A:
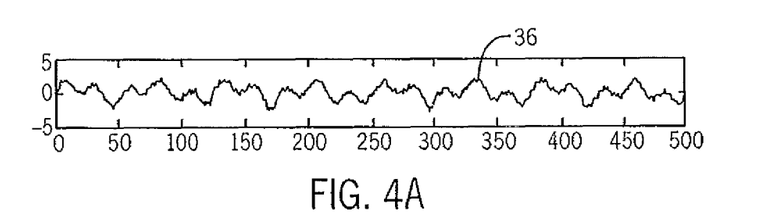
FIG. 4A depicts a waveform representing a pulse oximetry signal to be processed in accordance with aspects of the present technique.
Figure 4B:
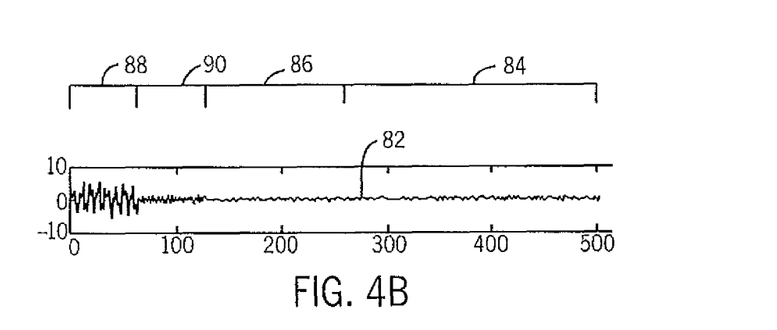
FIG. 4B depicts wavelet transformation of the waveform of FIG. 4A, in accordance with aspects of the present technique.
Figure 4C:
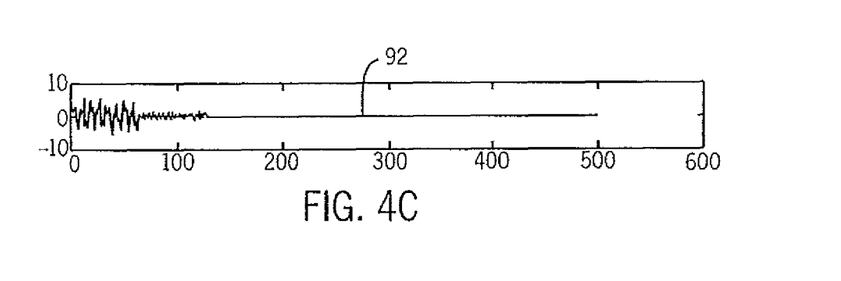
FIG. 4C depicts the wavelet vector of FIG. 4B modified to remove artifact signal, in accordance with aspects of the present technique.
Figure 4D:
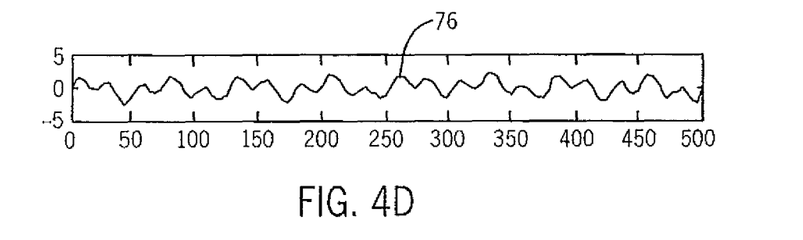
FIG. 4D depicts an output waveform reconstructed from the modified wavelet coefficients of FIG. 4C, in accordance with aspects of the present technique.

Referring now to FIGS. 4A-4D, example waveforms representative of the technique set forth in FIG. 3 are provided for the purpose of illustration. FIG. 4A depicts an oximetry signal 36, as provide in FIG. 3. The signal 36 of FIG. 4A contains artifacts to be compensated. FIG. 4B depicts a three-stage wavelet decomposition 82 of the original signal 36. The three-stage decomposition 82 includes a first high-passed component 84. The first low-passed component was further decomposed to yield a second high-passed component 86 and a second low-passed component that was in turn subsequently decomposed to generate a third low-passed component 88 and a third high-passed component 90. The third low-passed component 88 represents the approximation data for the original signal while the first, second, and third high-passed components 84, 86, 90 represent different levels of detail. FIG. 4C depicts the modified wavelet vector 92 after artifact compensation on the three-stage decomposition 82. In this example, the first and second low-passed bands 84 and 86 correspond to the identified artifact 64 and are set to zero (i.e. removed) in the modified wavelet vector 92, as depicted. The modified wavelet vector 92 provides the wavelet coefficients 72 that may be reconstructed, such as by an inverse wavelet transform, to generate a modified signal 76, such as the depicted output waveform. Artifacts present in the original signal 36 are compensated for in the modified signal 76. The modified signal 76 may be provided to subsequent processes for the determination of physiological characteristics of interest, such as blood oxygen saturation, pulse rate and so forth.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to pulse oximetry, but also to other physiological monitor outputs as well.

What is claimed is:

1. A method for processing a physiological signal, the method performed on a processing component and comprising the acts of:
   independently, identifying one or more artifacts in a physiological signal and performing one or more multi-resolution decompositions on the physiological signal to generate two or more decomposition products;
   compensating for the one or more artifacts in the two or more decomposition products to generate modified decomposition products;
   generating an artifact-compensated signal based on the modified decomposition products;
   processing the artifact-compensated signal at a monitor to derive one or more physiological characteristics of interest; and
   displaying the one or more physiological characteristics on the monitor.

2. The method of claim 1, comprising displaying the artifact-compensated signal on the monitor.

3. The method of claim 1, wherein the physiological characteristics comprise one or more of blood oxygen saturation, pulse rate, tissue water fraction, or tissue or blood carbon dioxide levels.

4. The method of claim 1, comprising locating portions of the two or more decomposition products that correspond to the identified artifacts.

5. The method of claim 4, wherein the two or more decomposition products comprise wavelet coefficients, and wherein compensation for artifacts comprises altering the values of the portions of the wavelet coefficients that correspond to artifacts.

6. A method for processing a signal using one or more of a sensor, a cable, or a monitor of a monitoring system comprising the acts of:
   decomposing the signal based on at least frequency characteristics of the signal to generate a plurality of coefficients;
   independently processing the signal to identify one or more artifacts within the signal;

setting the value of one or more coefficients corresponding to the one or more artifacts to zero to generate modified coefficients; and generating a modified signal based on the modified coefficients.

7. The method of claim 6, comprising displaying a waveform based on the modified signal on the monitor.

8. The method of claim 6, comprising processing the modified signal at a downstream device to derive one or more physiological characteristics of interest.

9. The method of claim 8, comprising displaying the physiological characteristics on the monitor.

10. The method of claim 8, comprising providing an audible or visual notification based on a value of the one or more physiological characteristics.

11. The method of claim 6, wherein the decomposition of the signal is based on time characteristics of the signal as well as frequency characteristics.

12. A physiological monitoring system, comprising:
a sensor configured to generate a physiological signal;
a monitor configured to receive a form of the physiological signal from the sensor; and
one or more processing components disposed in one of the sensor, the monitor, or in a cable connecting the sensor and the monitor, wherein the one or more processing components are configured to identify one or more artifacts in the physiological signal and, in parallel with the act of identification, to perform one or more multi-resolution decompositions on the physiological signal to generate two or more decomposition products, to modify respective values of portions of the two or more decomposition products corresponding to the identified artifacts to generate modified decomposition products, and to reconstruct the modified decomposition products to generate an artifact-compensated signal.

13. The system of claim 12, wherein the one or more processing components are further configured to process the artifact-compensated signal to derive one or more physiological characteristics of interest.

14. The system of claim 12, wherein the monitor is configured to display
one or more physiological characteristics derived from the artifact-compensated signal.

15. The system of claim 12, wherein the two or more decomposition products are characterized by time and frequency.

16. The system of claim 12, wherein the two or more decomposition products comprise wavelet coefficients, and wherein the one or more processing components are configured to modify respective values of the wavelet coefficients by setting the portions of the wavelet coefficients that correspond to artifacts to zero.

17. A monitor, comprising:
one or more processing components configured to receive a physiological signal generated by a sensor, to identify one or more artifacts in the received physiological signal, to perform one or more wavelet decompositions on the received physiological signal to generate a plurality of wavelet coefficients in parallel with identifying the one or more artifacts, to modify values of one or more of the wavelet coefficients based on the identified artifacts to generate modified coefficients, and to reconstruct the modified decomposition products to generate an artifact-compensated signal.

18. The monitor of claim 17, wherein the one or more processing components are configured to transmit the artifact compensated signal to a monitor which is not configured to perform artifact compensation.

19. The monitor of claim 17, wherein the wavelet coefficients are characterized by time and frequency.

20. The monitor of claim 17, wherein modifying values of the wavelet coefficients comprises setting values for some of the wavelet coefficients to zero.

* * * * *